US00PP28661P3

(12) United States Plant Patent
Meilland

(10) Patent No.: US PP28,661 P3
(45) Date of Patent: Nov. 21, 2017

(54) FLORIBUNDA ROSE PLANT NAMED 'MEIRIANSOIS'

(50) Latin Name: *Rosa hybrida*
Varietal Denomination: Meiriansois

(71) Applicant: THE CONARD-PYLE COMPANY, West Grove, PA (US)

(72) Inventor: Alain A. Meilland, Antibes (FR)

(73) Assignee: THE CONARD-PYLE COMPANY, West Grove, PA (US)

( * ) Notice: Subject to any disclaimer, the term of this patent is extended or adjusted under 35 U.S.C. 154(b) by 93 days.

(21) Appl. No.: 14/756,071

(22) Filed: Jul. 29, 2015

(65) Prior Publication Data

US 2017/0034972 P1 Feb. 2, 2017

(51) Int. Cl.
*A01H 5/02* (2006.01)

(52) U.S. Cl.
USPC ..... Plt./142

(58) Field of Classification Search
USPC ..... Plt./101, 141, 142
See application file for complete search history.

*Primary Examiner* — Susan McCormick Ewoldt
*Assistant Examiner* — Karen Redden
(74) *Attorney, Agent, or Firm* — Buchanan Ingersoll & Rooney PC

(57) ABSTRACT

A new and distinct Floribunda rose plant is provided that commonly commences blooming early in the season and forms abundantly and substantially continuously attractive red and white very double blossoms. The growth habit is compact and bushy. Strong vegetation is formed. The vegetation is dense and bears a glossy aspect on the upper surface. During observations to date the tolerance to diseases has been good, particularly with respect to Oidium. The plant is well suited for providing attractive ornamentation in the landscape.

1 Drawing Sheet

Figures 1, 2, 3, 4, 5, 6, 7, 8, 9, 10, 11, 12, 13, 14:
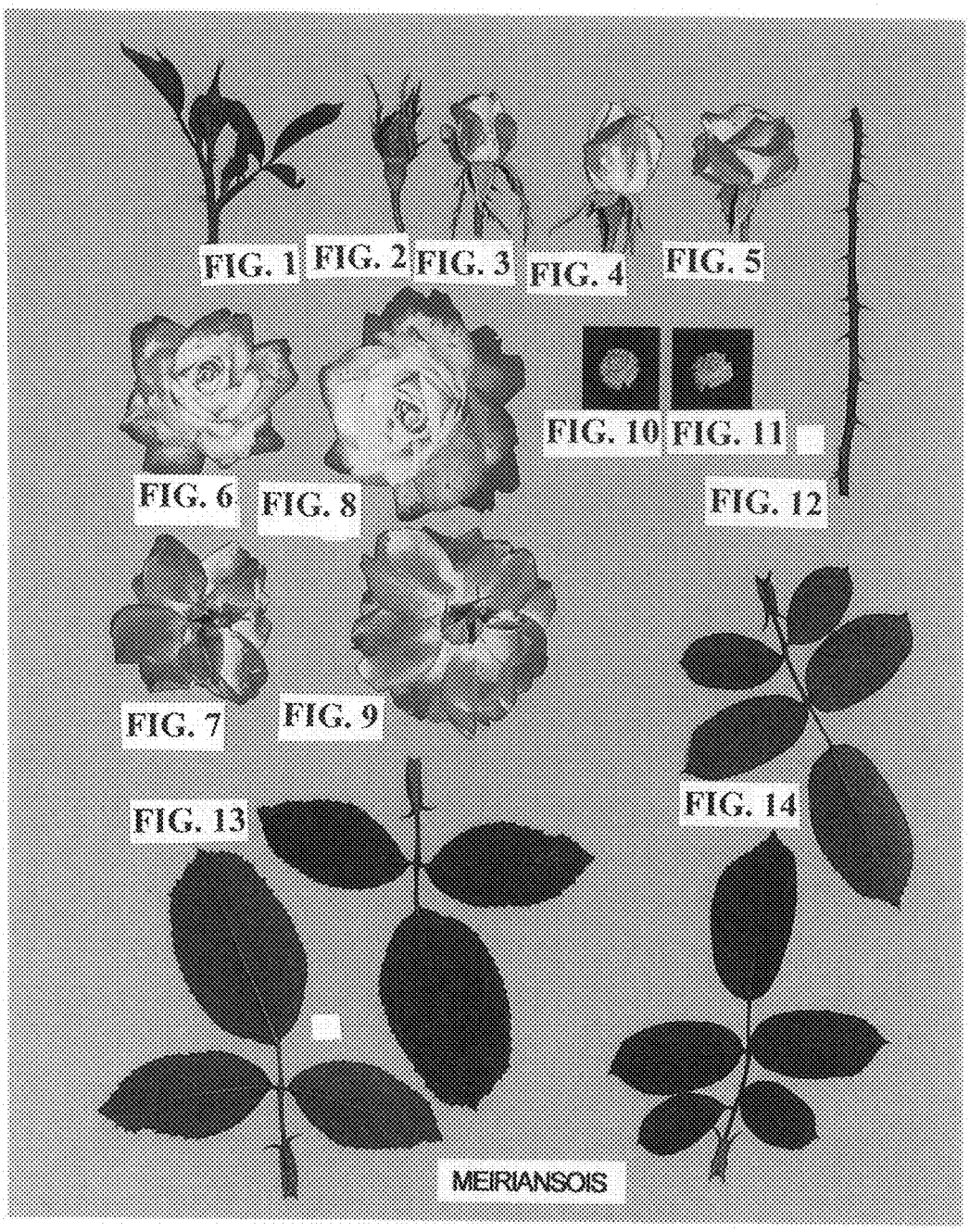

Botanical/commercial classification: *Rosa hybrida*/Floribunda Rose Plant.

Varietal denomination: cv. Meiriansois.

SUMMARY OF THE INVENTION

The new variety of *Rosa hybrida* Floribunda rose plant was created by artificial pollination wherein two parents were crossed which previously had been studied in the hope that they would contribute the desired characteristics. The female parent (i.e., the seed parent) was the product of the cross of the 'Meichoiju' variety (non-patented in the United States) and the 'Meikiji' variety (U.S. Plant Pat. No. 7,785). The male parent (i.e., the pollen parent) was the 'Radtko' variety (U.S. Plant Pat. No. 16,202).

The parentage of the new variety can be summarized as follows:

('Meichoiju'×'Meikiji')×'Radtko'.

The seeds resulting from the above pollination were sown and small plants were obtained which were physically and biologically different from each other. Selective study resulted in the identification of a single plant of the new variety.

It was found that the new Floribunda rose plant of the present invention:

(a) displays a compact and bushy growth habit with vigorous vegetation,
(b) forms in abundance on a substantially continuous basis attractive red and white very double blossoms,
(c) exhibits dense dark green foliage with a glossy aspect on the upper surface that contrasts nicely with the blossom coloration, and (d) is particularly well suited for providing attractive ornamentation in the landscape.

The blooming tends to be very floriferous. Blooming commonly commences early in the season and commonly is substantially continuous. Tolerance to diseases to date has been observed to be good, particularly with respect to Oidium.

The new variety well meets the needs of the horticultural industry and can be grown to advantage in parks and gardens where attractive ornamentation is to be provided.

The new variety can be readily distinguished from its ancestors. For instance, The 'Meichoiju' variety forms pink blossoms of uniform coloration. The 'Meikiji' variety forms French Rose edged with Rose Bengal blossoms having approximately 25 to 30 petals on average. The 'Radtko' variety forms blossoms of substantially uniform red coloration commonly having approximately 23 petals on average. The seed parent ('Meichoiju'×'Meikiji') displays flowers with larger diameter than that of the new variety.

The new variety has been found to undergo asexual propagation in France by a number of routes, including budding, grafting, and the use of cuttings. Asexual propagation by the above-mentioned techniques at Le Cannet des Maures, Var, France, has shown that the characteristics of the new variety are stable and are strictly transmissible by such asexual propagation from one generation to another. Accordingly, the new variety undergoes asexual propagation in a true-to-type manner.

The new variety has been named 'Meiriansois'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately one and one-half years of age and were observed during July while growing outdoors on *Rosa laxa* understock at Le Cannet des Maures, Var, France.

FIG. 1—illustrates a specimen of a young shoot;

FIG. 2—illustrates a specimen of a floral bud at the opening of the sepals;

FIG. 3—illustrates a specimen of a floral bud wherein the sepals are more fully open;

FIG. 4—illustrates a specimen of a floral bud at the opening of the petals;

FIG. 5—illustrates a specimen of a flower in the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates specimens of leaves with three leaflets—plan view—upper surface (right) and—under surface (below); and FIG. 14—illustrates specimens of leaves with five leaflets—plan view—upper surface (below) and—under surface (above).

DETAILED BOTANICAL DESCRIPTION

The chart used in the identification of the colors is that of The Royal Horticultural Society (R.H.S. Colour Chart). The description is based on the observation of one and one-half year-old plants during July while growing outdoors during July on *Rosa laxa* rootstock at Le Cannet des Maures, Var, France.

Class: Floribunda.

Plant:

*Growth habit*.—Compact and bushy.

*Vegetation*.—Strong.

*Height*.—Commonly near 1 m on average.

*Width*.—Commonly near 1 m on average.

Branches:

*Color*.—Young stems: near Yellow-Green Group 146C, and more or less suffused with Greyed-Purple Group 178A. Adult wood: near Yellow-Green Group 146A.

*Thorns*.—On young stems — long prickles: Configuration: with an oval base. Quantity: approximately 12 on average on a stem length of 10 cm. Length: approximately 0.7 to 1 cm on average. Color: near Greyed-Purple Group 178A. On young stems — short prickles: Configuration: generally oval. Quantity: approximately 15 on average on a stem length of 10 cm. Length: approximately 1 mm on average. Color: near Greyed-Purple Group 178A. On adult stems — long prickles: Configuration: slightly curved downwards on the upper surface and slightly concave on the under surface with an oval base. Quantity: approximately 9 on average on a stem length of 10 cm. Length: approximately 1 to 1.3 cm on average. Color: near Greyed-Orange Group 177A and 177B.

Leaves:

*Stipules*.—Adnate, pectinate, rather broad, approximately 2.5 cm in length on average, approximately 8 mm in width on average, near Green Group 138B on the upper surface, and near Green Group 138B on the under surface.

*Petioles*.—Upper surface: near Greyed-Purple Group 178A in coloration. Under surface: near Greyed-Purple Group 176C in coloration. Length: commonly approximately 4 to 4.5 cm on average. Diameter: commonly near 0.1 to 0.2 cm on average. Texture: non-glandular on the upper surface, and with a few small prickles on the under surface.

*Rachis*.—Upper surface: near Green Group 138C in coloration. Under surface: near Green Group 138B in coloration. Diameter: commonly near 0.1 to 0.15 cm on average. General appearance: dense.

*Leaflets*.—Number: 3, and most often 5 and 7. Shape: generally elliptical with a cuspidate tip and a rounded base. Size: the terminal leaflets commonly are approximately 6.5 cm in length on average, and approximately 4 cm in width on average. Serration: slightly denticulate, small and single (as illustrated). Texture: physically firm and leathery with a glossy upper surface. Color: (young foliage): Upper surface: near Yellow-Green Group 147A and 147B commonly with near Greyed-Purple Group 178A at the edges and on the venation. Under surface: near Yellow-Green Group 148B commonly with some Greyed-Purple Group 178A. Color (adult foliage): Upper surface: near Green Group 137A. Under surface: near Green Group 138A.

Inflorescence:

*Number of flowers*.—Commonly approximately 2 to 8 blossoms per stem.

*Peduncle*.—Smooth, approximately 6.5 cm in length on average, approximately 2 mm in diameter on average, and near Green Group 138B and commonly more or less suffused with near Greyed-Purple Group 178A.

*Sepals*.—Upper surface: tomentose and near Green Group 138C in coloration. Under surface: smooth and near Green Group 138B in coloration. Shape: longish and narrow, and somewhat upright at the base with some narrow extensions commonly having lengths of approximately 1 cm on average. Size: approximately 2.1 cm in length on average, and approximately 8 mm in width at the widest point on average. Number: typically 5 on average.

*Buds*.—Shape: substantially conical. Size: small. Length: approximately 2 cm on average. Width: approximately 1.7 cm at the widest point on average. Color as calyx breaks: Upper surface: near Yellow-White Group 158C and commonly more or less margined with Red-Purple Group 58B and 58C. Under surface: near Yellow-White Group 158C and commonly more or less margined with Red-Purple Group 58B and 58C.

*Flower*.—Shape: cup-shaped. Diameter: approximately 8 cm on average. Color (in the course of opening): Upper surface: near Yellow-White Group 158C, more or less suffused with near Red-Purple Group 62D, and more or less margined primarily on the external petals with Red-Purple Group 58B and 58C. Under surface: near Yellow-White Group 158C, more or less suffused with near Red-Purple Group 62D, and more or less margined primarily on the external petals with Red-Purple Group 58B and 58C. Color (open flower): Upper side: near Yellow-White Group 158C, more or less suffused with Red-Purple Group 58B and 58C. Under side: near Yellow-White Group 158C, more or less suffused with Red-Purple Group 58B and 58C. Fragrance: none detected. Petal number: approximately 42 on average under normal growing conditions. Petal shape: with a substantially cuspidate tip and an obtuse base. Petal texture: leathery and somewhat firm. Petal length: approximately 3.7 cm on average. Petal width: approximately 3 cm on average. Petal arrangement: imbricated, and without petaloids. Petal drop: good with the petals commonly detaching cleanly before drying. Stamen number: approximately 37 on average. Anthers: regularly arranged around the styles, approximately 1 mm in size on average, and near Yellow Group 2D in coloration. Filaments: approximately 3 mm in length on average, and near Yellow-Green Group 150D in coloration. Pollen: none available for observation. Pistils: approximately 51 on average. Stigmas: approximately 1 mm in size on average, and near Yellow Group 2D in coloration. Styles: approximately 2 mm in length on average, and near Red Group 45C in coloration. Receptacle: smooth, funnel-shaped in longitudinal section, approximately 8 mm in length on average, approximately 7 mm in width on average at the widest point, and near Green Group 138A and 138B in coloration. Hip/seed: none observed.

Development:

*Vegetation*.—Strong.

*Blooming*.—Early season: typically from May to November, very abundant, and substantially continuous.

*Tolerance to diseases*.—Good, particularly with respect to Oidium.

The new 'Meiriansois' variety has not been observed under all possible environmental conditions to date. Accordingly, it is possible that the phenotypic expression may vary somewhat with changes in light intensity and duration, cultural practices, and other environmental conditions.

I claim:

1. A new and distinct Floribunda rose plant characterized by the following characteristics:

(a) displays a compact and bushy growth habit with vigorous vegetation, (b) forms in abundance on a substantially continuous basis attractive red and white very double blossoms, (c) exhibits dense dark green foliage with a glossy aspect on the upper surface that contrasts nicely with the blossom coloration, and (d) is particularly well suited for providing attractive ornamentation in the landscape;

substantially as shown and described.

* * * * *

MEIRIANSOIS